United States Patent [19]
Iijima

[11] Patent Number: 6,132,046
[45] Date of Patent: *Oct. 17, 2000

[54] OPHTHALMOLOGIC APPARATUS

[75] Inventor: Hiroshi Iijima, Tokyo, Japan

[73] Assignee: Kabushiki Kaisha Topcon, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/303,543

[22] Filed: May 3, 1999

[30] Foreign Application Priority Data

May 8, 1998 [JP] Japan ................................. 10-125941

[51] Int. Cl.[7] ...................................................... A61B 3/14
[52] U.S. Cl. ............................................................. 351/208
[58] Field of Search ..................................... 351/204, 205, 351/206, 208, 209, 211, 212, 221, 210, 239, 243, 244; 348/78; 396/51

[56] References Cited

U.S. PATENT DOCUMENTS 5,621,457  4/1997  Ishiwaka et al. ........................ 348/78
5,668,622  9/1997  Charbonnier et al. .................. 351/209
5,682,224  10/1997  Takagi et al. .
5,987,151  11/1999  Akashi ...................................... 351/210

FOREIGN PATENT DOCUMENTS

8-173385  7/1996  Japan .
10-80397  3/1998  Japan .

*Primary Examiner*—George Manuel
*Attorney, Agent, or Firm*—Armstrong, Westerman, Hattori, McLeland & Naughton

[57] ABSTRACT

In an ophthalmologic apparatus which can start a measurement or a photographing operation with respect to an eye to be examined by suitably making an automatic alignment with a cornea of the eye as a center, When a diseased eye is to be measured, slight reflected light (e.g., cornea scattering light) except for reflected light from a vertex of the cornea of the eye is interrupted by an XY alignment detecting stop even when this slight reflected light is detected by a position detecting sensor. Accordingly, since no slight reflected light is almost incident to a light quantity detecting sensor, the XY alignment light quantity detecting circuit does not output an alignment completion signal to a control circuit. Thus, the control circuit performs a control operation such that the measurement or the photographing operation with respect to the eye is not performed.

10 Claims, 7 Drawing Sheets

OPHTHALMOLOGIC APPARATUS

BACKGROUND OF THE INVENTION

1. Field of the Invention

The present invention relates to an ophthalmologic apparatus having an alignment function for automatically starting the measurement of an intraocular pressure or a photographing operation with respect to an eye to be examined.

2. Description of Related Art

An ophthalmologic apparatus having a so-called automatic alignment function is conventionally known. In the ophthalmologic apparatus, alignment target light is projected onto an eye to be examined of an examinee, and light reflected by a cornea of the eye is guided to a position detecting sensor by an optical system for receiving reflected light. A measuring unit is automatically aligned with the eye on the basis of an output of the position detecting sensor.

In such an ophthalmologic apparatus, an examiner makes a rough alignment between a measurement optical axis of the measuring unit and the cornea of the eye by operating a joy stick, etc. while the examiner observes through a finder or a monitor. After the rough alignment is completed, a measurement optical axis of the measuring unit is automatically aligned with a vertex of the cornea of the eye on the basis of the output of the position detecting sensor. Thereafter, when a shifting quantity between the measurement optical axis of the measuring unit and the cornea vertex of the eye is equal to or smaller than a predetermined value by the automatic alignment, the measurement of the intraocular pressure, etc. or the photographing operation with respect to the eye is automatically started.

However, when the eye is a diseased eye such as a cataract, there is a case in which disturbance light except for the reflected light from cornea is entered to the position detecting sensor. In this case, there was a case in which no automatic alignment with the cornea vertex of the eye can be suitably made and the automatic measurement is started in a position shifted from the cornea vertex of the eye. Therefore, no exact measurement value could be obtained and the obtained measurement value was not reliable. Further, it was required to make the measurement again, which increases a burden to the examinee.

SUMMARY OF THE INVENTION

In view of the above circumstances, the present invention has been made, and an object of the present invention is to provide an ophthalmologic apparatus which can start a measurement or a photographing operation with respect to an eye to be examined by making a suitable automatic alignment with a cornea of the eye as a center.

To solve the above problems, according to the present invention, there is provided an ophthalmologic apparatus for aligning an apparatus body with an eye to be examined, characterized by comprising: an alignment target projecting system for projecting alignment target light to a cornea of the eye; first detecting means for detecting an alignment state of the eye by making a cornea reflected light flux of the alignment target light incident on a position detecting element which can detect the position of a center of gravity of the incident light flux; second detecting means for detecting the alignment state of the eye by making the cornea reflected light flux incident on a light quantity detecting element which can detect a light quantity of the incident light flux, through a stop which determines an alignment completion position; actuating means for actuating the apparatus body; and determining means for determining, in accordance with detected results of the first detecting means and the second detecting means, whether the alignment by the actuating means is completed or not.

According to the ophthalmologic apparatus of the present invention, it is characterized in that a measurement or a photographing operation with respect to the eye is started in accordance with the detected result of the second detecting means.

According to the ophthalmologic apparatus of the present invention, it is characterized in that the determining means determines that no alignment is completed by the actuating means when the first detecting means outputs the detected result representing the alignment completion and the second detecting means outputs the detected result representing that no alignment is completed.

According to the ophthalmologic apparatus of the present invention, it is characterized in that the ophthalmologic apparatus further comprises informing means for informing an examiner of a determined result of the determining means.

According to the ophthalmologic apparatus of the present invention, it is characterized in that an operation of the actuating means is stopped in accordance with the determined result of the determining means.

DETAILED DESCRIPTION OF THE PREFERRED EMBODIMENTS

Now descriptions will be made of embodiments of the present invention with reference to the accompanying drawings.

Figure 1:
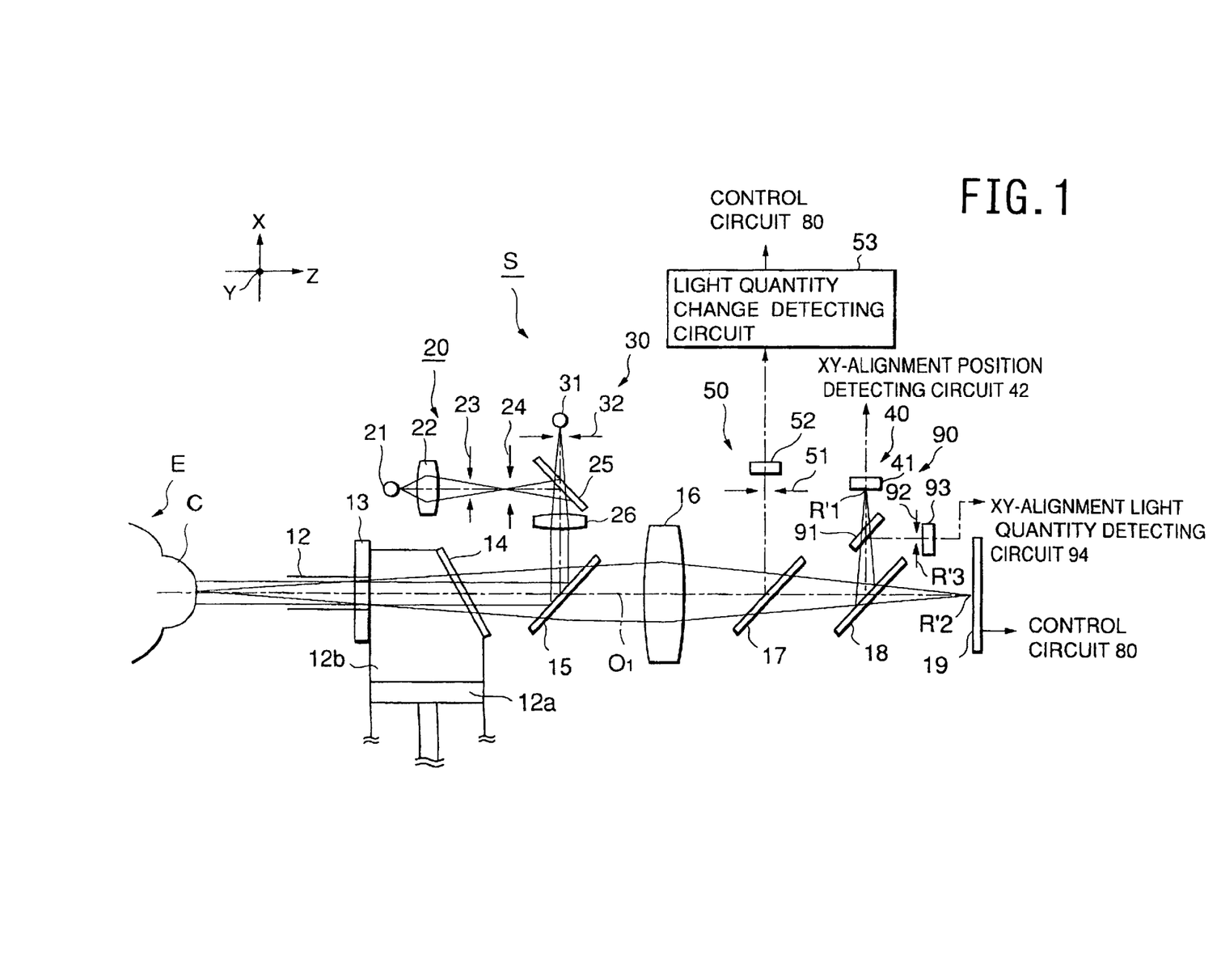
FIG. 1 is a plan arrangement view of the schematic structure of an optical system of an intraocular pressure measuring apparatus as one example of an ophthalmologic apparatus in an embodiment of the present invention.
Figure 2:
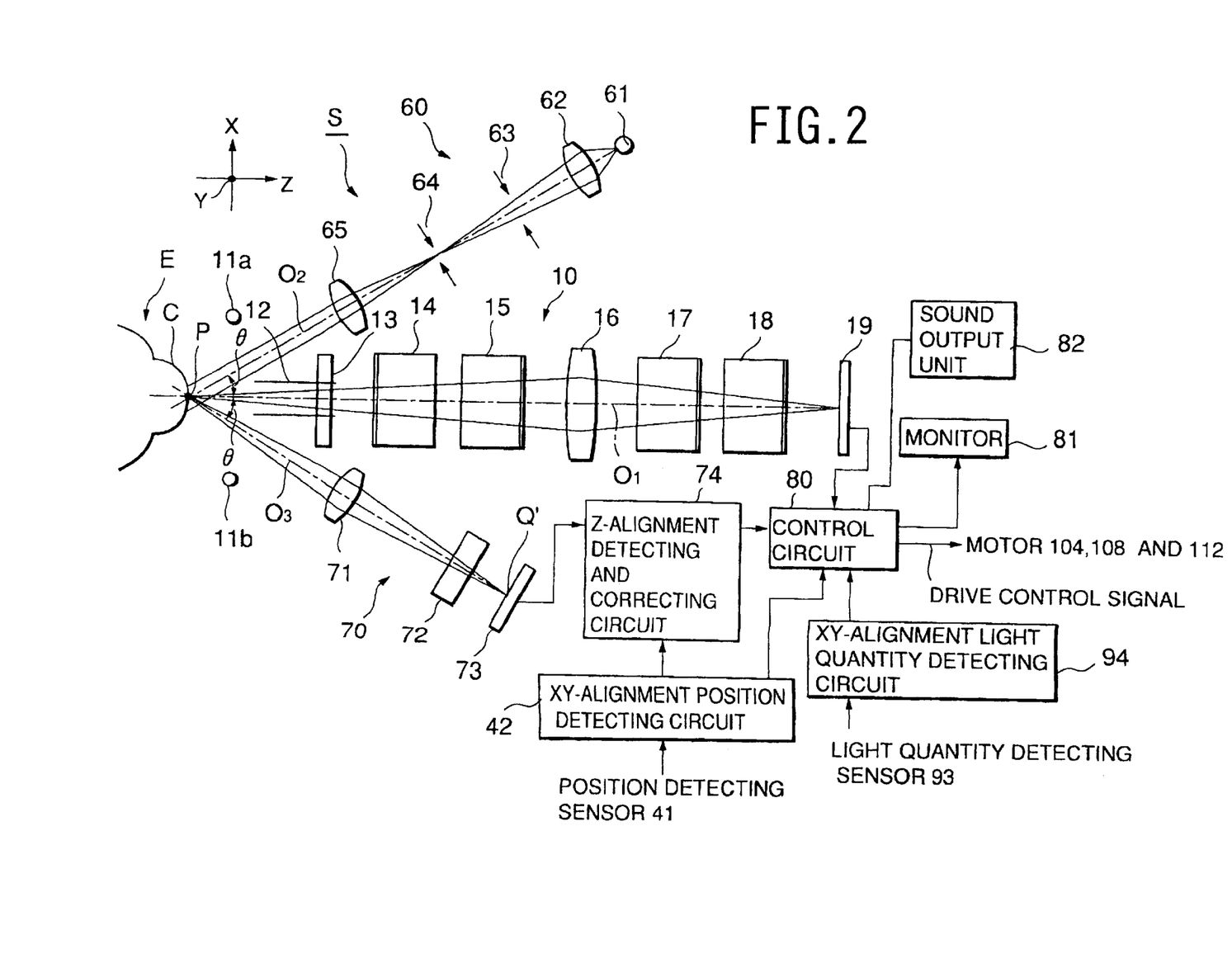
FIG. 2 is a side arrangement view of the schematic structure of the optical system of the intracular pressure measuring apparatus as one example of the ophthalmologic apparatus in the embodiment of the present invention.

FIG. 1 is a plan arrangement view of the schematic structure of an optical system of an intraocular pressure measuring apparatus as one example of an ophthalmologic apparatus in an embodiment of the present invention. FIG. 2 is a side arrangement view of the schematic structure of the optical system of the intraocular pressure measuring apparatus as one example of the ophthalmologic apparatus in the embodiment of the present invention.

In FIGS. 1 and 2, the ophthalmologic apparatus S in the embodiment of the present invention has, a front eye portion observing system 10 for observing a front portion of an eye E to be examined, and an XY alignment target projecting optical system 20 for projecting target light (XY alignment target light) to a cornea C of the eye E to be examined from its front face. This target light is used for alignment detection in XY directions (a vertical direction and a left-right direction) and is also used to detect a transfiguring quantity of the cornea of the eye E by spraying of the air for measuring an intraocular pressure. The ophthalmologic apparatus S also has a fixation mark projecting optical system 30 for projecting a fixing mark to the eye E. The ophthalmologic apparatus S also has a first XY alignment detecting optical system 40 for detecting the position relation in the XY directions between the ophthalmologic apparatus S and the cornea C by receiving reflected light of the XY alignment target light from the cornea C. The ophthalmologic apparatus S also has a cornea transfiguring quantity detecting optical system 50 for receiving the reflected light of the XY alignment target light from the cornea C and detecting the transfiguring quantity of the cornea C by spraying the air to the cornea C. The ophthalmologic apparatus S also has a Z-alignment target projecting optical system 60 for projecting target light (Z-alignment target light) for alignment detection in a Z-direction (forward-backward direction) from an oblique direction to the cornea C. The ophthalmologic apparatus S also has a Z-alignment detecting optical system 70 for receiving reflected light of the Z-alignment target light from the cornea C in a symmetrical direction with respect to an optical axis of the front eye portion observing optical system 10 and detecting the position relation in the Z-direction between the ophthalmologic apparatus S and the cornea C. The ophthalmologic apparatus S further has a second XY alignment detecting optical system 90 for receiving reflected light of the XY alignment target light from the cornea C and detecting the position relation in the XY directions between the ophthalmologic apparatus S and the cornea C.

The front eye portion observing optical system 10 is constructed by a plurality of front eye portion illuminating light sources 11a, 11b located on left-hand and right-hand sides of the eye E to be examined and directly illuminating a front eye portion, an air spraying nozzle 12 for spraying the air to the eye E at a measuring time of the intraocular pressure of the eye E, a front eye portion window glass 13, a chamber window glass 14, a half mirror 15, an objective lens 16, half mirrors 17, 18, and a charge coupled device (CCD) camera 19. These units are arranged on an optical axis O1. w When the intraocular pressure of the eye E is measured, the air within a cylinder 12b is compressed by a piston 12a and sprayed to the cornea C of the eye E through the air spraying nozzle 12. The piston 12a is operated by an air spraying unit (not shown). This air spraying unit is driven on the basis of outputs of an XY alignment light quantity detecting circuit 94 and a Z-alignment detecting and correcting circuit 74 described later.

A front portion image of the eye E illuminated by the front eye portion illuminating light sources 11a, 11b passes through inner and outer sides of the air spraying nozzle 12, and is transmitted through the front eye portion window glass 13, the chamber window glass 14, and the half mirror 15. The front eye portion image is then formed onto the CCD camera 19 transmitting through the half mirrors 17, 18 while this image is converged by the objective lens 16.

The XY alignment target projecting optical system 20 is constructed by a light source 21 for an XY alignment for emitting infrared light, a condenser lens 22, an aperture stop 23, a pinhole plate 24, a dichroic mirror 25, a projecting lens 26, the half mirror 15, the chamber window glass 14, and the air spraying nozzle 12. The projecting lens 26 is arranged on an optical path to focus the light on the pinhole plate 24.

Figure 3:
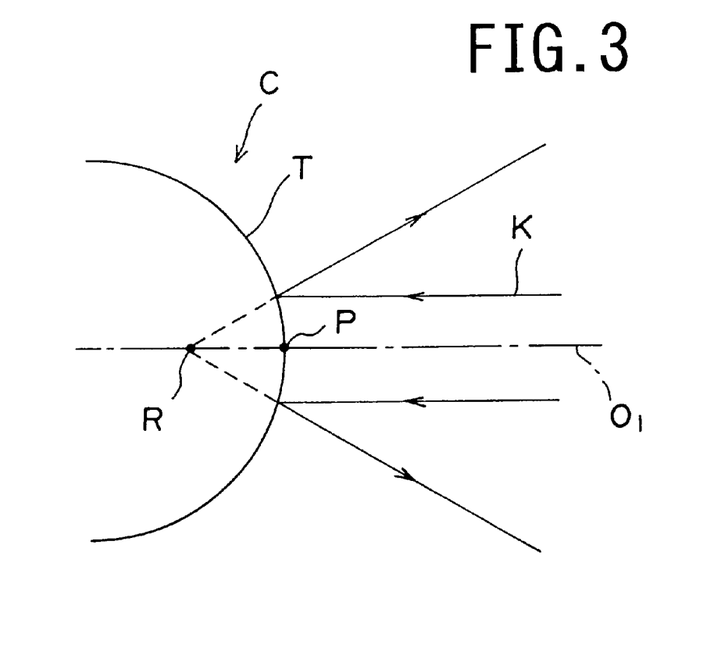
FIG. 3 is a view for explaining the reflection of alignment target light projected from a front face onto the cornea of an eye to be examined.

The infrared light emitted from the light source 21 for the XY alignment passes through the aperture stop 23 while the infrared light is converged by the condenser lens 22, and then guided to the pinhole plate 24. Light flux passing through the pinhole plate 24 is reflected by the dichroic mirror 25 and changed to parallel light flux by the projecting lens 26. After this light flux is then reflected by the half mirror 15, the light flux is transmitted through the chamber window glass 14 and passes through the interior of the air spraying nozzle 12 and forms XY alignment target light K as shown in FIG. 3. In FIG. 3, the XY alignment target light K is reflected by a cornea surface T so as to form a luminescent spot image R in an intermediate position between a vertex P of the cornea C and a center of curvature of the cornea C. The aperture stop 23 is arranged in a position conjugate to the vertex P of the cornea C with respect to the projecting lens 26. The XY alignment target light K is also used to detect the cornea transfiguration as described later.

The fixation mark projecting optical system 30 is constructed by a light source 31 for a fixation mark for emitting visible light, a pinhole plate 32, the dichroic mirror 25, the projecting lens 26, the half mirror 15, the chamber window glass 14, and the air spraying nozzle 12.

Light for the fixation mark emitted from the light source 31 is changed to parallel light flux by the projecting lens 26 through the pinhole plate 32 and the dichroic mirror 25. After the light flux is reflected by the half mirror 15, it is transmitted through the chamber window glass 14, and guided to the eye E passing through the interior of the air spraying nozzle 12. Accordingly, an examinee carefully looks at this fixation mark as a fixation target so that a viewing line is fixed.

The first XY alignment detecting optical system 40 is w constructed by the air spraying nozzle 12, the chamber window glass 14, the half mirror 15, the objective lens 16, half mirrors 17, 18, 91, a position detecting sensor 41 for detecting the position of a center of gravity of a luminescent spot image R1', and an XY alignment position detecting circuit 42. The second XY alignment detecting optical system 90 is constructed by the air spraying nozzle 12, the chamber window glass 14, the half mirror 15, the objective lens 16, the half mirrors 17, 18, 91, an XY alignment detecting stop 92, a light quantity detecting sensor 93, and the XY alignment light quantity detecting circuit 94.

Light flux is projected onto the cornea C by the XY alignment target projecting optical system 20 and reflected by the cornea surface T. The light flux passes through the interior of the air spraying nozzle 12 and is transmitted through the chamber window glass 14 and the half mirror 15. While the light flux is converged by the objective lens 16, One portion of the light flux is transmitted through the half mirror 17, and another portion of the light flux is reflected by the half mirror 18.

One portion of the light flux reflected by the half mirror 18 is transmitted through the half mirror 91 and thus forms a luminescent spot image R1' on the position detecting sensor 41. The XY alignment position detecting circuit 42 calculates the position relation in the XY directions between the ophthalmologic apparatus S and the cornea C on the basis of an output of the position detecting sensor 41, and outputs calculated results to a Z-alignment detecting and correcting circuit 74 and a control circuit 80.

The control circuit 80 outputs a drive control signal to motors 104, 108 described later on the basis of the calculated results. That is, the first XY alignment detecting optical system 40 can be used for an automatic alignment using an alignment driving mechanism described later. However, since the first XY alignment detecting optical system 40 detects the position of a center of gravity of an incident light flux, its detecting result includes an error when disturbance light is made incident on the first XY alignment detecting optical system 40. Accordingly, there is a defect in which no exact alignment detection in the XY directions can be performed.

The light flux reflected by the half mirror 91 passes through the XY alignment detecting stop 92 and forms a luminescent spot image R3' on the light quantity detecting sensor 93. The XY alignment detecting stop 92 is arranged in a position conjugate to a virtual image R formed on the cornea C by the XY alignment target projecting optical system 20 with respect to the objective lens 16. A size of the XY alignment detecting stop 92 is set such that a light quantity equal to or greater than a predetermined quantity is made incident on the light quantity detecting sensor 93 when a shifting quantity between the vertex of the cornea C and the optical axis O1 is reduced to such an extent that no measurement accuracy of the intraocular pressure is influenced by this shifting quantity. The XY alignment light quantity detecting circuit 94 determines on the basis of an output of the light quantity detecting sensor 93 whether the alignment in the XY directions is completed or not, and then outputs the determination result to the control circuit 80.

Since the second alignment detecting optical system 90 merely detects the incident light quantity by the light quantity detecting sensor 93, the second alignment detecting optical system 90 cannot detect shifting quantities of the alignment in the XY directions. Accordingly, the second alignment detecting optical system 90 merely detects in two values whether the alignment in the XY directions is completed or not. However, an exact alignment in the XY directions uninfluenced by disturbance light can be detected by an operation of the XY alignment detecting stop 92.

When the XY alignment position detecting circuit 42 outputs arithmetic results showing the completion of the XY alignment and the XY alignment light quantity detecting circuit 94 outputs determination result showing that no light quantity equal to or greater than the predetermined quantity is made incident on the XY alignment light quantity detecting circuit 94, the control circuit 80 makes a monitor 81 to display a message representing that the automatic alignment is impossible on the screen G of the monitor 81. Further, the control circuit 80 makes a sound output unit 82 to generate a warning sound or a voice message representing that the automatic alignment is impossible.

Figure 4:
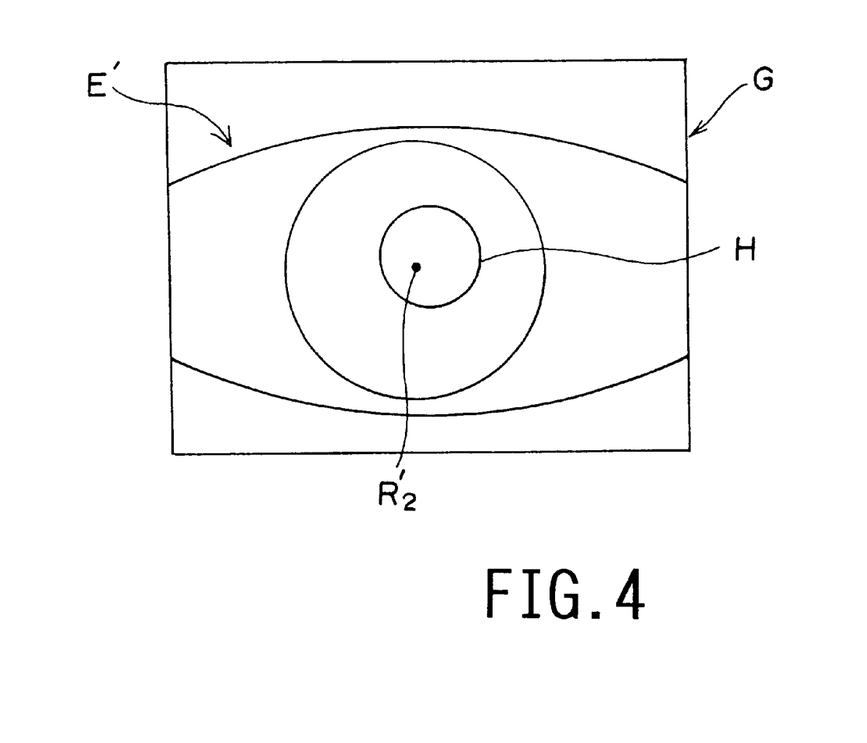
FIG. 4 is a view of a front portion image of a normal eye displayed on a screen of a monitor of the ophthalmologic apparatus in the embodiment of the present invention.

In contrast to this, the light flux reflected from the cornea C transmitting through the half mirror 18 forms a luminescent spot image R2' on the CCD camera 19. The CCD camera 19 outputs an image signal to the monitor 81 through the control circuit 80. Thus, as shown in FIG. 4, a front portion image E' of the eye E and the luminescent spot image R2' of the XY alignment target light are displayed on the screen G of the monitor 81. An alignment assistance mark H displayed on the screen G is generated by image generator (not shown).

Further, the light flux reflected by the half mirror 17 from the cornea C is guided to the cornea transfiguring quantity detecting optical system 50 and made incident on a transfiguring quantity detecting sensor 52 passing through a pinhole plate 51. The transfiguring quantity detecting sensor 52 is a light receiving sensor which can detect a light quantity such as a photodiode.

An output of the transfiguring quantity detecting sensor 52 is input to a light quantity change detecting circuit 53, to detect a change in the received light quantity in the transfiguring quantity detecting sensor 52 with the passage of time. This detecting result is output to the control circuit 80. The control circuit 80 calculates an intraocular pressure value of the eye to be examined on the basis of the detecting result and a pressure changing curve in the cylinder 12b.

The Z-alignment target projecting optical system 60 is constructed by a light source 61 for a Z-alignment for emitting infrared light, a condenser lens 62, an aperture stop 63, a pinhole plate 64, and a projecting lens 65 arranged on an optical path to focus the light on the pinhole plate 64. These units are arranged on an optical axis O2.

Figure 5:
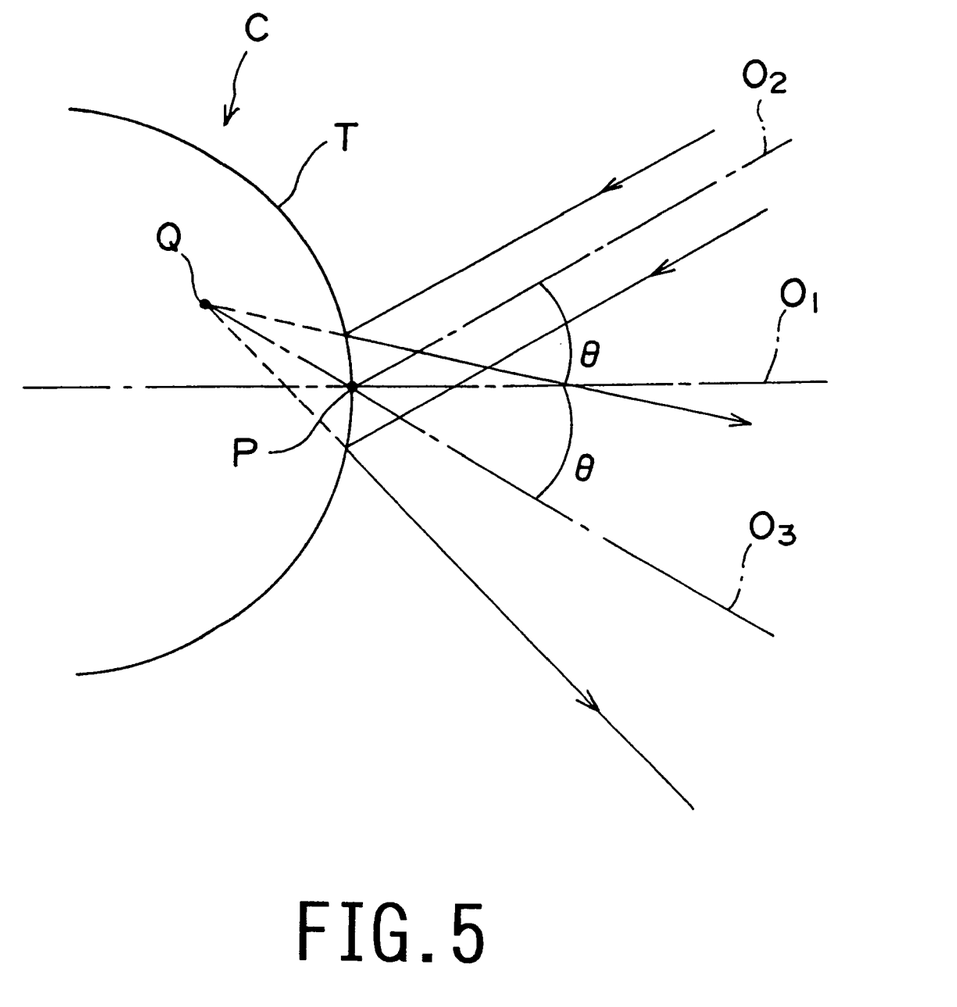
FIG. 5 is a view for explaining the reflection of the alignment target light projected onto the cornea of the eye from an oblique direction.

The infrared light emitted from the light source 61 for the Z-alignment is guided to the pinhole plate 64 passing through the aperture stop 63 while the infrared light is converged by the condenser lens 62. Light flux passing through the pinhole plate 64 is changed to parallel light flux by the projecting lens 65 and guided to the cornea C. As shown in FIG. 5, the light flux is then reflected by the cornea surface T so as to form a luminescent spot image Q. The aperture stop 63 is arranged in a position conjugate to the vertex P of the cornea C with respect to the projecting lens 65.

The Z-alignment detecting optical system 70 is constructed by an image forming lens 71, a cylindrical lens 72 having refractive power in a Y-direction, a detecting sensor 73, and a Z-alignment detecting and correcting circuit 74. These units are arranged on an optical axis O3.

Reflected light flux of Z-alignment target light projected by the Z-alignment target projecting optical system 60 from the cornea surface T forms a luminescent spot image Q' on the detecting sensor 73 through the cylindrical lens 72 while the light flux is converged by the image forming lens 71. The detecting sensor 73 is a light receiving sensor which can detect a position, for example, a line sensor or a position sensitive diode (PSD). An output of the detecting sensor 73 is output to the Z-alignment detecting and correcting circuit 74.

The luminescent spot image Q and the detecting sensor 73 have a conjugate position relation with respect to the image forming lens 71 in XZ planes. The cornea vertex P and the detecting sensor 73 have a conjugate position relation with respect to the image forming lens 71 and the cylindrical lens 72 in YZ planes. That is, the detecting sensor 73 has a conjugate relation to the aperture stop 63 (at this time, magnification is selected such that the size of an image of the aperture stop 63 is smaller than the size of the detecting sensor 73). Accordingly, the light flux reflected by the cornea surface T is efficiently entered to the detecting sensor 73 even when the position of the cornea C is shifted in the Y-direction. In a case wherein slit light extending in the Y-direction is projected to the cornea C, when the cornea C is shifted in the Y-direction as mentioned above, entire incident efficiency is reduced. However, the reflected light flux can be efficiently entered to the detecting sensor 73.

An output (alignment information in the XY directions) of the XY alignment position detecting circuit 42 is input to the Z-alignment detecting and correcting circuit 74, to exactly perform the alignment detection in the Z-direction without having any influence of shifts in alignment in the XY directions. Thus, Z-alignment information obtained by the detecting sensor 73 is corrected.

Figure 6A:
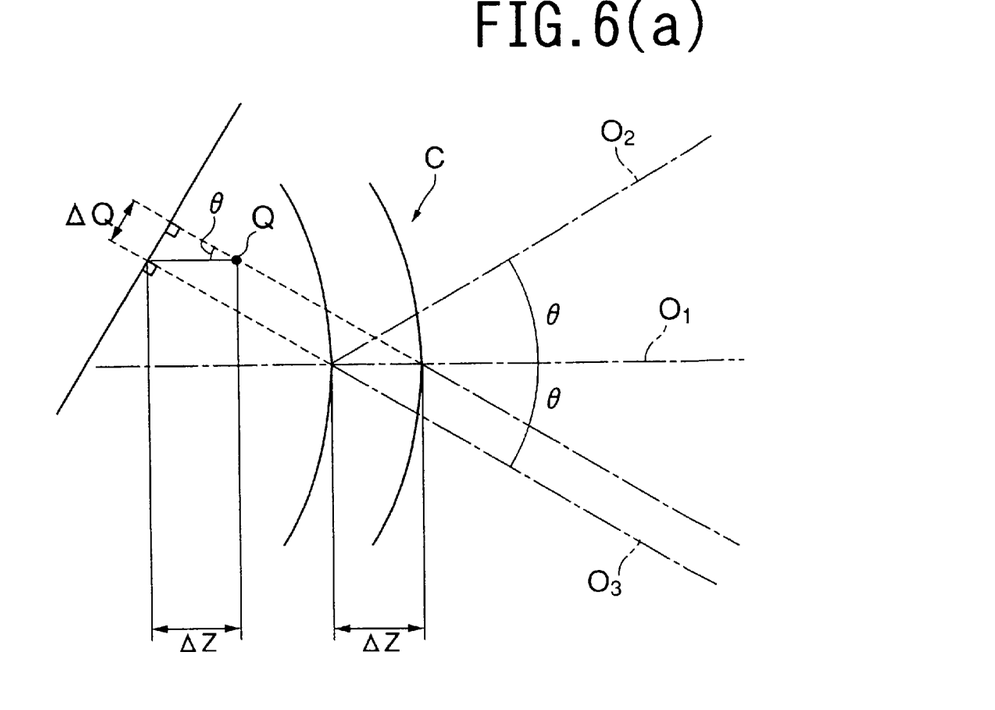
FIGS. 6(a) and 6(b) are views for explaining the relation of incidence and reflection of the alignment target light when a position of the cornea of the eye is shifted in a Z-direction and an X-direction.
Figure 6B:
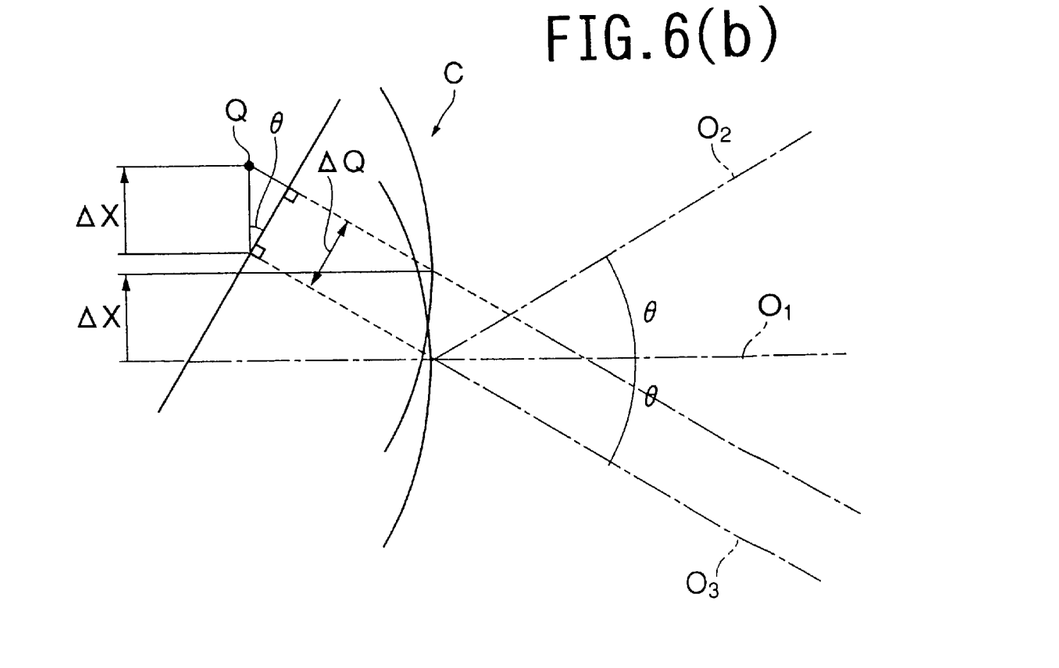

FIGS. 6(a) and 6(b) are views for explaining the relation of incidence and reflection of alignment target light when the position of the cornea of the eye to be examined is shifted. FIG. 6(a) shows a case wherein the position of the cornea is shifted in the Z-direction. FIG. 6(b) shows a case wherein the position of the cornea is shifted in the X-direction.

As shown in FIG. 6(a), when the position of the cornea C is shifted by $\Delta Z$ in the Z-direction, the position of a luminescent spot image Q' on the detecting sensor 73 is moved by $\Delta Z \times \sin\theta \times m$. Here, $\theta$ is an angle formed by the optical axis O1 and the optical axis O2, and an angle formed by the optical axis O1 and the optical axis O3. Further, m is an image forming magnification of the Z-alignment detecting optical system 70. Accordingly, in a case wherein the positions of the cornea C are suitable in the XY directions and the position thereof is shifted only in the Z-direction, if a shifting quantity (moving quantity) $\Delta Q'$ from a reference position of the luminescent spot image Q' on the detecting sensor 73 is obtained, the shifting quantity $\Delta Z$ of the position of the cornea C can be easily calculated by $\Delta Q'/(\sin\theta \times m)$ However, as shown in FIG. 6(b), when the position of the cornea C is shifted by $\Delta X$ in the X-direction, the position of the luminescent spot image Q' on the detecting sensor 73 is also moved by $\Delta X \times \cos\theta \times m$. Therefore, when the position of the cornea C is shifted in each of the Z-direction and the X-direction, the position of the luminescent spot image Q' on the detecting sensor 73 is moved by $(\Delta Z \times \sin\theta \times m)+(\Delta X \times \cos\theta \times m)$. Accordingly, in this case, the Z-alignment detecting and correcting circuit 74 calculates the position relation (shifting quantity $\Delta Z$) in the Z-direction between the ophthalmologic apparatus S and the cornea C on the basis of the moving quantity $\Delta Q'$ of the luminescent spot image Q' on the detecting sensor 73 and the shifting quantity $\Delta X$ output from the XY alignment position detecting circuit 42 in accordance with the following equation (1), and outputs the shifting quantity $\Delta Z$ as the calculated result to the control circuit 80.

$$\Delta Z = (\Delta Q' - \Delta X \cos\theta \times m)/(\sin\theta \times m) \quad (1)$$

The control circuit 80 outputs a drive control signal to a motor 112 described later on the basis of the calculated result.

Figure 7:
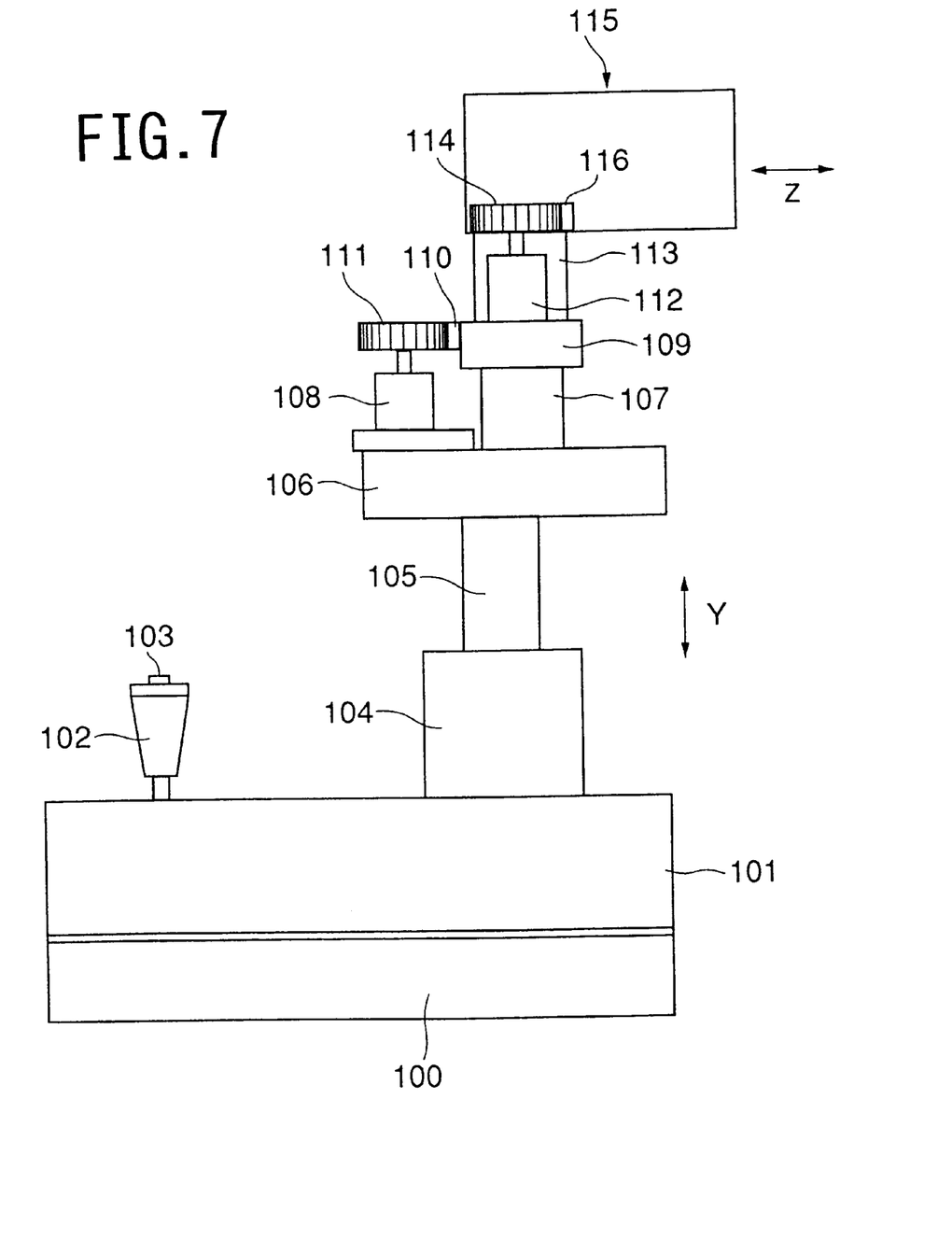
FIG. 7 is a side view of the structure of an alignment mechanism of the ophthalmologic apparatus in the embodiment of the present invention.
Figure 8:
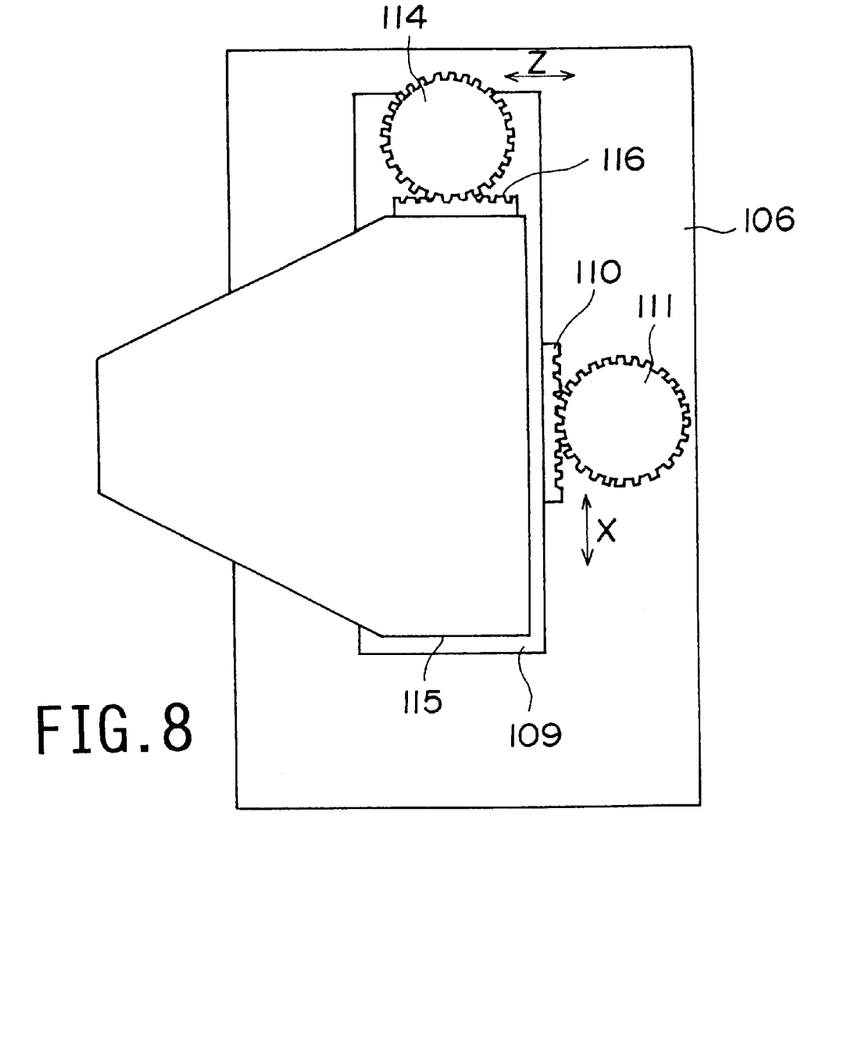
FIG. 8 is a plan view of the structure of the alignment mechanism of the ophthalmologic apparatus in the embodiment of the present invention.

FIG. 7 is a side view of the structure of an alignment mechanism of the ophthalmologic apparatus in the embodiment of the present invention. FIG. 8 is a plan view of the structure of the alignment mechanism of the ophthalmologic apparatus in the embodiment of the present invention. In FIGS. 7 and 8, the alignment mechanism of the ophthalmologic apparatus in the embodiment of the present invention is arranged on a frame 101 movable forward, backward, leftward and rightward on a fixing base 100 in which power source (not shown) is built, by operating a control lever 102 such as a joy stick. The alignment mechanism is constructed by a vertical (Y-direction) actuating mechanism, a horizontal (X-direction) actuating mechanism, and a forward-backward (Z-direction) actuating mechanism. A manual switch 103 is arranged at the control lever 102 and used as a measurement starting switch at a manual measurement mode.

The vertical actuating mechanism is constructed by a motor 104 for raising and lowering movements provided at an upper portion of the frame 101, and a support 105 held by the frame 101 so as to be movable vertically (in the Y-direction) (namely, able to be raised and lowered). The motor 104 and the strut 105 are connected to each other by a pinion and a rack (not shown). The support 105 is vertically moved by the motor 104. A table 106 is arranged at an upper end of the support 105.

The horizontal actuating mechanism is constructed by a support 107 and a motor 108 provided on the table 106, a table 109 slidably held leftward and rightward (in the X-direction) at an upper end of the support 107, a rack 110 arranged at one end of the table 109, and a pinion 111 provided onto an output shaft of the motor 108. The pinion 111 is engaged with the rack 110.

The forward-backward actuating mechanism is constructed by a motor 112 and a support 113 provided onto an upper portion of the table 109, a pinion 114 provided onto an output shaft of the motor 112, and an apparatus body case 115 arranged at an upper portion of the support 113. The apparatus body case 115 is slidably held forward and backward (in the Z-direction). A rack 116 is provided at a side portion of the apparatus body case 115 and engaged with the pinion 114. The optical system shown in FIGS. 1 and 2 is stored inside the apparatus body case 115.

The motors 104, 108 and 112 are controlled by a control signal output from the control circuit 80. The motor 104 is used to automatically alignment the apparatus body case 115 in the Y-direction. The motor 108 is used to automatically alignment the apparatus body case 115 in the X-direction. The motor 112 is used to automatically alignment the apparatus body case 115 in the Z-direction. Each of the motors 104, 108 and 112 is constructed by using a stepping motor (pulse motor) which can perform position control.

An operation of the ophthalmologic apparatus in the embodiment of the present invention will next be explained.

When a healthy normal eye is to be measured, an operator moves the frame 101 by operating the control lever 102 so as to position a front eye portion image E' at the center of a screen G of the monitor 81 shown in FIG. 4 while the operator observes the front eye portion image E' on the screen G of the monitor 81. When reflected light of the cornea C is incident to the position detecting sensor 41 and the detecting sensor 73, XY alignment information and Z-alignment information are respectively output from the XY alignment position detecting circuit 42 and the Z-alignment detecting and correcting circuit 74 to the control circuit 80.

The control circuit 80 outputs a control signal to the motors 104, 108 and 112 on the basis of the output XY alignment information and the output Z-alignment information. Thus, while the apparatus body case 115 storing the optical system shown in FIGS. 1 and 2 is moved in the XY directions and the Z-direction, the automatic alignment is made, to move a luminescent spot image R1' to a desirable position on the position detecting sensor 41, i.e., to move a luminescent spot image R2' to a focusing position within the range of an alignment assistance mark H on the screen G of the monitor 81.

When the vertex of the cornea C approximately corresponds to the optical axis O1, light having a light quantity equal to or greater than a predetermined quantity is incident to the light quantity detecting sensor 93. Accordingly, an alignment completion signal is output from the XY alignment light quantity detecting circuit 94 to the control circuit 80. When the control circuit 80 receives the alignment completion signal from the XY alignment light quantity detecting circuit 94 and also receives a Z-direction alignment completion signal from the Z-alignment detecting and correcting circuit 74, the control circuit 80 operates an air spraying unit (not shown), so that the air is sprayed toward the cornea C from the air spraying nozzle 12. Thus, a transfiguring quantity of the cornea C at a spraying time of the air is detected by the cornea transfiguring quantity detecting optical system 50. Thereafter, an intraocular pressure value of the eye E is calculated by using a well-known method on the basis of an air spraying pressure when the transfiguring quantity is equal to a predetermined transfiguring quantity.

An alignment state of the ophthalmologic apparatus S to the eye E can be detected on the basis of the XY alignment information output from the XY alignment position detecting circuit 42 and the Z-alignment information output from the Z-alignment detecting and correcting circuit 74, and the detecting results can be also displayed in the monitor 81.

Figure 9:
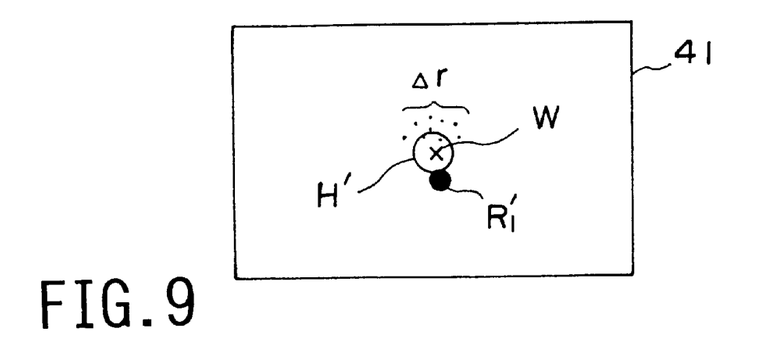
FIG. 9 shows a state of incident light on a position detecting sensor when a diseased eye is measured.

In contrast to this, when a diseased eye is to be measured, as shown in FIG. 9, slight cornea scattering light Δr caused by the roughness of a cornea surface by a cornea operation is incident to the position detecting sensor 41 in addition to the luminescent spot image R1' from the cornea C of the eye E. Therefore, the XY alignment information output from the XY alignment position detecting circuit 42 includes an error based on the cornea scattering light Δr.

That is, when there is such cornea scattering light Δr, the position detecting sensor 41 calculates the position W of a center of gravity of the luminescent spot image R1' and the cornea scattering light Δr. The XY alignment position detecting circuit 42 calculates a shifting quantity of the optical axis O1 and the vertex of the cornea C of the eye E on the basis of the position W of the center of gravity of the luminescent spot image R1' and the cornea scattering light Δr, and outputs calculated results to the control circuit 80.

Accordingly, as shown in FIG. 9, when the luminescent spot image R1' does not correspond to the optical axis O1, but the position W of the center of gravity of the luminescent spot image R1' and the cornea scattering light Δr is located within an alignment area H' corresponding to the alignment assistance mark H and corresponds to the optical axis O1, the XY alignment position detecting circuit 42 recognizes this corresponding position as an XY alignment completion position in error.

However, in this case, one portion or all portions of a luminescent spot image R3' are interrupted by the XY alignment detecting stop 92, so that no sufficient light quantity is incident to the light quantity detecting sensor 93. Accordingly, since the detecting light quantity of the light quantity detecting sensor 93 is equal to or smaller than the predetermined light quantity, the XY alignment light quantity detecting circuit 94 determines that XY alignment is not completed.

Thus, when the XY alignment position detecting circuit 42 outputs calculated results representing the XY alignment completion and the XY alignment light quantity detecting circuit 94 outputs determined results representing that light quantity equal to or greater than the predetermined light quantity is not incident to the light quantity detecting sensor 93, the control circuit 80 makes the monitor 81 to display that the automatic alignment is impossible on the screen G of the monitor 81. Further, the control circuit 80 makes the sound output unit 82 to generate a warning sound or a voice message representing that the automatic alignment is impossible. An operator switches an automatic alignment mode to a manual alignment mode by a mode changing switch (not shown) on the basis of this display. Further, the automatic alignment mode can be also automatically switched to the manual alignment mode with generation of the warning sound by the control circuit 80.

When the automatic alignment mode is switched to the manual alignment mode, the control circuit 80 does not output a control signal to the motors 104, 108 and 112 in response to an output of the XY alignment position detecting circuit 42 and an output of the Z-alignment detecting and correcting circuit 74. Accordingly, the apparatus body case 115 storing the optical system shown in FIGS. 1 and 2 does not move automatically. The operator moves the frame 101 forward, backward, leftward and rightward by operating the control lever 102 while the operator observes the screen G of the monitor 81 shown in FIG. 9. Further, the operator moves the table 106 upward and downward by rotating the control lever 102. Each of switches (not shown) is turned on in accordance with a rotating direction of the control lever 102 and the control circuit 80 operates the motor 104 at normal revolution or reverse revolution on the basis of a switching signal of each of these switches.

When the operator manually positions reflected light R2" from the vertex of the cornea C of the eye E within the alignment assistance mark H, reflected light having a light quantity equal to or greater than a predetermined light quantity from the vertex of the cornea C is incident to the light quantity detecting sensor 93. At this time, the output (moving quantity ΔQ') of the Z-alignment detecting and correcting circuit 74 is supplied to the control circuit 80. Here, since the alignment in the XY directions is completed, it is not necessary to make a correction by the XY alignment information output from the XY alignment position detecting circuit 42. Thus, ΔZ is calculated on the basis of the moving quantity ΔQ' in accordance with the following equation (2).

$$\Delta Z = \Delta Q'/(\sin \theta \times m) \tag{2}$$

Here, when the output of the XY alignment light quantity detecting circuit 94 and the output of the Z-alignment detecting and correcting circuit 74 become values in desirable ranges, the control circuit 80 operates the air spraying unit so that the air is sprayed from the air spraying nozzle 12 to the cornea C. Thus, a transfiguring quantity of the cornea C at the air spraying time is detected by the cornea transfiguring quantity detecting optical system 50. Thereafter, an intraocular pressure value of the eye E is calculated by using a well-known calculating equation from an air spraying pressure when the transfiguring quantity is equal to a desirable transfiguring quantity.

In the above description, a non-contact type intraocular pressure meter is explained as an example. However, the present invention can be also applied to another ophthalmologic apparatus, for example, a cornea endothelium cell image photographing apparatus.

As mentioned above, according to the present invention, a detecting stop and a light quantity detecting sensor are arranged such that only reflected light from the vertex of the cornea of the eye to be examined is detected and no disturbance light except for this reflected light is detected. Also, the automatic alignment is suitably made at a center of the cornea of the eye. Accordingly, a measurement or a photographing operation with respect to the eye to be examined can be efficiently started.

For example, a more suitable automatic alignment can be made in the case of an intraocular pressure measuring apparatus, so that a more exact intreaocular pressure value can be obtained. Further, it is not necessary to measure the intraocular pressure again, thus a burden to an examinee can be reduced.

What is claimed is:

1. An ophthalmologic apparatus for aligning an apparatus body with an eye to be examined, comprising:

an alignment target projecting system for projecting alignment target light to a cornea of the eye;

first detecting means for detecting an alignment state of the eye with a position detecting element which can detect the position of a center of gravity of an incident light flux;

second detecting means for detecting the alignment state of the eye with a light quantity detecting element which can detect a light quantity of the incident light flux, through a stop which determines an alignment completion position;

actuating means for actuating the apparatus body; and determining means for determining, in accordance with detected results of the first detecting means and the second detecting means, whether the alignment by the actuating means is completed or not.

2. The ophthalmologic apparatus of claim 1, wherein a measurement or a photographing operation with respect to the eye is started in accordance with the detected result of the second detecting means.

3. The ophthalmologic apparatus of claim 2, wherein the determining means determines that no alignment is completed by the actuating means when the first detecting means outputs the detected result representing the alignment completion and the second detecting means outputs the detected result representing that no alignment is completed.

4. The ophthalmologic apparatus of claim 2, wherein the ophthalmologic apparatus further comprises informing means for informing an examiner of a determined result of the determining means.

5. The ophthalmologic apparatus of claim 2, wherein an operation of the actuating means is stopped in accordance with the determined result of the determining means.

6. The ophthalmologic apparatus of claim 1, wherein the determining means determines that no alignment is completed by the actuating means when the first detecting means outputs the detected result representing the alignment completion and the second detecting means outputs the detected result representing that no alignment is completed.

7. The ophthalmologic apparatus of claim 6, wherein the ophthalmologic apparatus further comprises informing means for informing an examiner of a determined result of the determining means.

8. The ophthalmologic apparatus of claim 6, wherein an operation of the actuating means is stopped in accordance with the determined result of the determining means.

9. The ophthalmologic apparatus of claim 1, wherein the ophthalmologic apparatus further comprises informing means for informing an examiner of a determined result of the determining means.

10. The ophthalmologic apparatus of claim 1, wherein an operation of the actuating means is stopped in accordance with the determined result of the determining means.

* * * * *